United States Patent

Hayes et al.

[11] Patent Number: 5,614,719
[45] Date of Patent: Mar. 25, 1997

[54] FLUID MONITORING

[76] Inventors: Alan J. Hayes, 25 Echo Hill, Royston Hertfordshire, United Kingdom, SG7 5NT/UK; Allen W. Mabbitt, 5A Park Avenue, Bedford, United Kingdom, MK40 2JY/UK

[21] Appl. No.: 256,854
[22] PCT Filed: Feb. 8, 1993
[86] PCT No.: PCT/GB93/00263
§ 371 Date: Jul. 28, 1994
§ 102(e) Date: Jul. 28, 1994
[87] PCT Pub. No.: WO93/16371
PCT Pub. Date: Aug. 19, 1993

[30] Foreign Application Priority Data

Feb. 7, 1992 [GB] United Kingdom ............... 9202647

[51] Int. Cl.$^6$ ............................................. G01N 21/35
[52] U.S. Cl. ................................. 250/343; 250/345
[58] Field of Search ................................ 250/343, 345, 250/338.3, 338.5, 339.12

[56] References Cited

U.S. PATENT DOCUMENTS

| | | | |
|---|---|---|---|
| 3,005,097 | 10/1961 | Hummel | 250/345 |
| 5,155,545 | 10/1992 | Rinke | 250/345 |
| 5,160,843 | 11/1992 | Lehto | 250/343 |

FOREIGN PATENT DOCUMENTS

| | | | |
|---|---|---|---|
| 0214688 | 10/1984 | Germany | 250/345 |
| 60-129645 | 7/1985 | Japan | 250/345 |

*Primary Examiner*—David P. Porta
*Assistant Examiner*—Richard Hanig
*Attorney, Agent, or Firm*—William Lloyd Clayborn; John M. Cone

[57] ABSTRACT

Apparatus and method of monitoring fluid presence, wherein electomagnetic radiation sources (1, 2) provide respective reference and sample beams (12, 22), the wavelength of the radiation preferably being matched with that of the absorption spectrum of a fluid to be monitored. A first reference cell (13), containing a reference sample of the fluid to be monitored, has the reference beam (12) passed through it, whilst a second, sample cell (33) containing any working sample of the fluid to be monitored, has both the reference and sample beams (12, 22) passed through it. Subsequently, the reference and sample beams are detected independently of each other to provide respective signals representative thereof, which signals are then compared to determine the presence, and preferably also the concentration, of any sample fluid in the second cell. The invention can also be used in the analysis of fluids and has particular application in the monitoring of gases in a dirty environment, such as, a mine or other high particle-contaminated space.

24 Claims, 1 Drawing Sheet

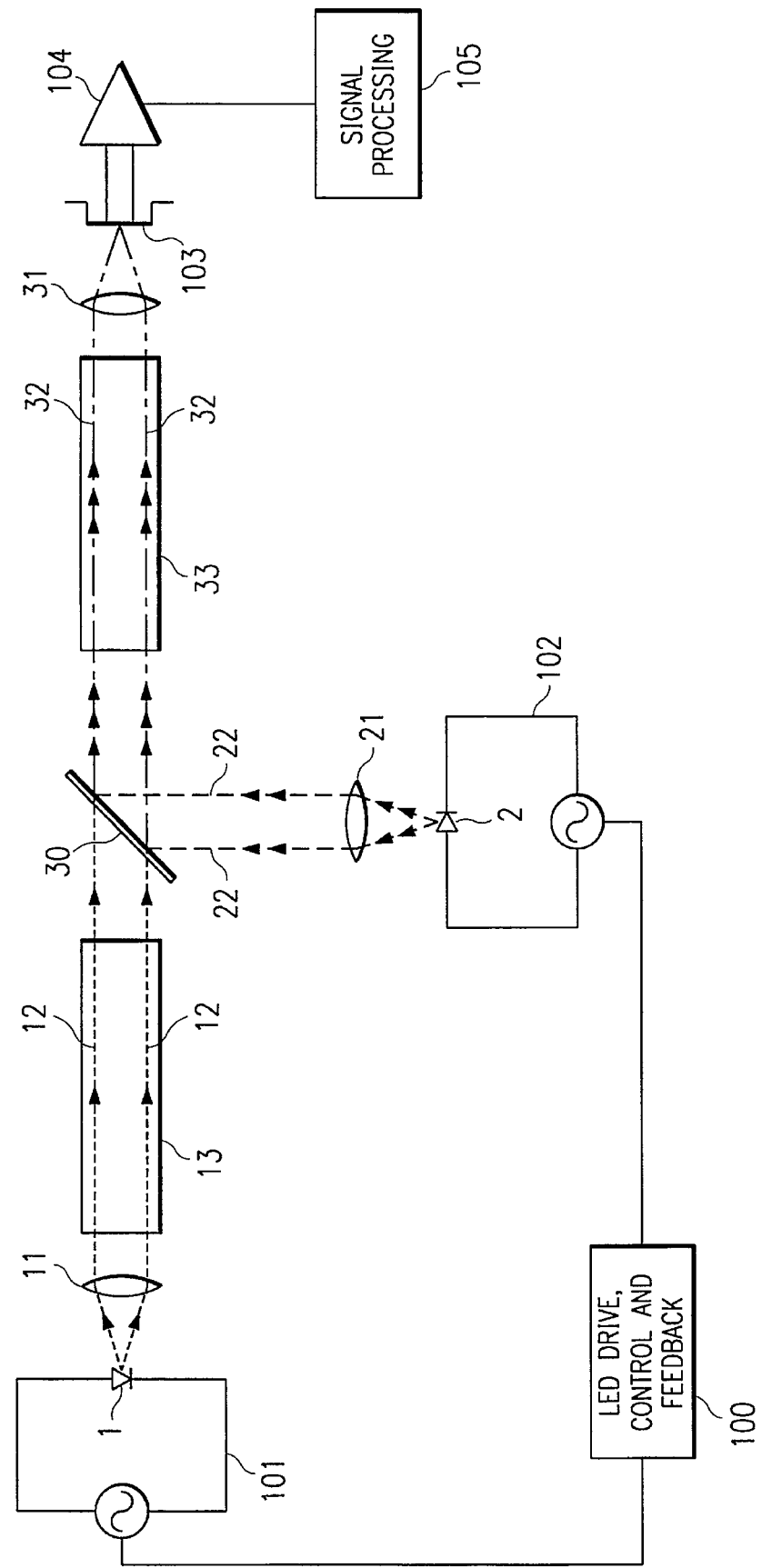

FLUID MONITORING

DESCRIPTION

This invention relates to apparatus for and a method of monitoring for the presence of a fluid and is especially, but not exclusively, related to the monitoring of a gas in a dirty environment, such as, a mine or other high particle-contaminated environment.

Such inventive apparatus and method may also be used for the detection and/or qualitative and/or quantitative analysis of a fluid.

Any fluid exhibits a characteristic light absorption spectrum which can be used to monitor the presence and quantify the amount of the fluid in a given sample. The precise configurations of such absorption spectra vary from fluid to fluid but generally consist of both fundamental and derived overtone absorption bands. Thus, a choice of wavelength region for a fluid to be monitored is usually available. Additionally, some fluids also exhibit regular comb-like absorption spectra structures around their primary absorption lines, examples of such fluids being methane, carbon monoxide and oxygen.

A conventional gas monitoring arrangement consists of a light source, wavelength band filter and an appropriate detector plus a gas sample cell through which light from the source is passed.

If a DC system of monitoring is employed, then a reference beam is required for calibration purposes. In a "dirty" environment, such as, a coal mine, there is considerable scope for measurement errors, in that it is difficult to ensure that the sample and reference beams are equally affected by any contamination.

Also, such known arrangements tend to lack sensitivity and, hence, are not suitable for use in monitoring low level fluid leaks.

It is an object of the present invention to provide apparatus for and a method of monitoring for the presence of a fluid which overcome, or at least substantially reduce, the disadvantages associated with the known fluid monitoring arrangements discussed above.

Accordingly, one aspect of the invention resides in fluid monitoring apparatus comprising electromagnetic radiation sources arranged to provide respective reference and sample beams of electromagnetic radiation, the wavelength of the electromagnetic radiation preferably being matched with that of the absorption spectrum of a fluid to be monitored, a first cell which contains a reference sample of the fluid to be monitored and through which the reference beam of electromagnetic radiation is passable, a second cell which is capable of containing a working sample of the fluid to be monitored and through which both the reference and sample beams of electromagnetic radiation are passable, means arranged to detect the reference and sample beams independently of each other after they have passed through the second cell and to provide respective signals representative of the independently-detected beams, and means arranged to compare said signals in order to determine the presence, and preferably also the concentration, of any working sample of fluid to be monitored in the second cell.

In accordance with a second aspect of the invention, there is provided a method of monitoring for the presence of a fluid, comprising passing through a first cell containing a reference sample of the fluid to be monitored a reference beam of electromagnetic radiation, passing through a second cell capable of containing a working sample of the fluid to be monitored the reference beam of electromagnetic radiation and a sample beam of the electromagnetic radiation, the wavelength of the radiation preferably being matched with that of the absorption spectrum of the fluid to be monitored, detecting the reference and sample beams independently of each other after they have passed through the second cell, providing respective signals representative of the independently detected beams and comparing said signals to determine the presence, and preferably also the concentration, of any working sample of fluid to be monitored in the second cell.

The reference and sample beams may be of any suitable form, as long as they can be detected independently of each other. For example, they may be of continuous wave, sinusoidal form or pulsed, such as square wave, in which case, they are preferably out of phase with each other. In this manner, a single detection means can be used to detect successive portions or pulses of the out-of-phase beams.

Separate and alternately activated electromagnetic radiation sources may be used to generate respective reference and sample beams, preferred sources being light emitting diodes (LEDs).

Also, a single common detector is preferred for detecting the reference and sample beams independently of each other.

Alternatively, the reference and sample beams may be of AC form at different frequencies, in which case, the detector means is arranged to detect the different frequencies independently of each other, for instance, by phase-locking techniques. This latter arrangement tends to increase the sensitivity and stability of the inventive apparatus and method.

Preferably, and as mentioned above, the electromagnetic radiation sources are light emitting diodes (LEDs) whose emission wavelengths are, advantageously, matched to be complimentary with the absorption spectrum of the fluid to be monitored. Alternatively, any other sources of electromagnetic radiation may be employed, with the wavelength of the radiation preferably being matched to that of the absorption spectrum of the fluid to be monitored. However, it has been found that LEDs are preferred, in view of their robustness for use in rigorous working environments, as well as their wavelength emission bands which tend to be more narrow than those of gas/filament bulbs which have been used previously in known arrangements and which emit generally "white" radiation.

In a preferred embodiment of the inventive apparatus and method, the sample and reference beams from respective modulated LEDs are collimated initially and are subsequently combined, out of phase with each other, after the reference bee has passed through the reference cell containing the fluid to be monitored.

Preferably, the detector means for detecting the two beams independently of each other, such as, the portions or pulses of the out-of-phase LED-sourced reference and sample bees, comprises a photodiode, or other suitable detector, such as, a photoconductive or pyroelectric detector or any combination thereof. The corresponding signals representative of the detected reference and sample beams are preferably amplified before being subjected to AC signal enhancement and subsequent comparison processing.

In the preferred embodiment also, two LEDs may be driven by out of phase current pulses or by AC signals at different frequencies.

Although the inventive apparatus and method are mainly applicable to the monitoring of fluids, such as, hazardous gases, they may also be employed in the qualitative and quantitave analysis of both gases and liquids.

The second, sample cell may be at least partially filled with the sample fluid to be monitored by relying upon diffusion of the fluid, such as, gas diffusion, through it in situ or by having the fluid pumped through it either in situ or at a remote location. Alternatively, the second, sample cell may be in the form of a working or living space, such as, a mine gallery, chemical or gas processing/handling plant, room or the like, in which a gas is present and is to be monitored.

In any event, because the reference and sample beams of electromagnetic radiation pass along substantially the same path through the fluid contained in the sample cell prior to their detection, any contamination in the sample cell affects both beams to an equal extent and, therefore, does not affect the accuracy of the inventive apparatus and/or method.

The signal outputs from the detector may be subjected to signal processing, such as that referred to above, namely, AC signal enhancement, to improve the signal to noise ratios thereof.

The various components of the inventive apparatus may be selected to be specific to any desired absorbing fluid, that is to say, either a gas or liquid, to be monitored, detected or analysed by the appropriate choice of reference fluid and working wavelength of the electromagnetic radiation of the reference and sample beams.

Moreover, apparatus and method in accordance with the invention may be modified for use with multiple reference beams each with its own reference cell. The cells may contain different or mixtures of different gases or different concentrations of different or mixtures of different gases to be detected, monitored or analysed, with each reference beam being passed through the sample cell in combination with the sample beam. Additionally, each reference beam may be modulated in the time or frequency domain in such a way as to allow a beam or beams unaffected by the contents of the sample cell to be isolated, thus enabling the detection, monitoring or analysing of different gases or gas mixtures.

In order that the invention may be more fully understood, a preferred embodiment in accordance therewith will now be described by way of example and with reference to the accompanying drawing which is a schematic diagram of gas monitoring apparatus for use in a hazardous gas environment.

Referring to the drawing, there is shown apparatus for monitoring the presence of methane in a hazardous environment, such as a mine, which apparatus comprises a first source of electromagnetic radiation in the form of a light emitting diode (LED) 1 arranged to emit infra-red radiation at a wavelength of approximately 3 microns which is compatible with the wavelength absorption spectrum of methane gas.

A second source of electromagnetic radiation is in the form of another LED 2 which is also arranged to emit infra-red radiation at a wavelength of approximately 3 microns.

The infra-red radiation emitted by the LED 1 is collimated at 11 to provide a reference beam 12 which is passed through a first, reference cell 13 containing a reference sample of methane gas of a sufficient concentration to absorb from the beam 12 substantially the whole of the wavelengths of the absorption spectrum of methane.

The collimated infra-red radiation beam 12 passing through the reference cell 13 has its intensity reduced by absorption in the absorption bands of the reference sample of methane gas.

Infra-red radiation emitted by the second LED 2, is also collimated but at 21 to provide a sample beam 22.

An LED, control and feedback unit 100 is connected between the respective driver circuits 101, 102 for the LEDs 1 and 2.

This unit 100 is arranged to drive the LEDs 1 and 2, such that their respective reference and sample beams 12, 22 are out of phase with each other.

A beam combiner 30 of any suitable form is provided between the reference cell 13 and the sampling cell 33 through which the combined but out-of-phase reference and sample beams 12, 22 pass, such combined beams being represented by beam 32.

This combined beam 32 is passed through the sample cell 33 containing any methane gas which may be received therein by diffusion or pumping of the ambient atmosphere into the cell 33. In any event, because the combined beam 32 passes through the sample cell 33 prior to detection thereof, as will be described hereinbelow, any contamination in the sample cell 33, for instance, by the presence of coal dust or other fine particulate material therein or other gases with absorption spectra within the wavelength band of the beam 32, affects both the reference and sample beams 12, 22 to an equal extent and, thus, does not affect accuracy of detection and any associated measurement of the concentration of any methane in the cell 33 but does not affect resolution.

Because absorption of the infra-red radiation of the reference beam 12 has already taken place in the reference cell 13, no further absorption from that beam takes place in the sample cell 33 by any methane gas being monitored therein. On passing through the sample cell 33, the intensity of the sample beam 22, however, is reduced by the absorption of the relevant infra-red wavelengths by any methane gas being monitored therein. Such reduction in intensity of the sample beam 22 is proportional to the amount of methane gas present in the sample cell 33. It is a logarithmic relationship but is effectively linear for the path lengths of the beams 12, 22, 32 and absorption coefficients involved.

Any reduction in the intensity of the sample beam 22 is calibrated against known standards to provide a quantitative analysis (concentration) of methane gas present in the sample cell 33 at that particular time.

After passing through the sample cell 33, the combined beam 32, comprising the out-of-phase reference and sample beams 12, 22, is focussed at 31 on to an infra-red detector 103 whose response speed is sufficiently fast to detect successive portions (pulses) of the out of phase reference and sample beams to provide respective signals representative thereof. Such signals are then amplified at 104 and passed to a signal processing unit 105.

Using AC signal enhancement techniques, the two signals representative of the detected reference and sample beams are processed to provide a comparison therebetween, thereby providing an indication of the presence of any methane gas in the cell 33, as well as a qualitative and/or quantitative analysis of any such gas contained therein.

The infra-red detector 103 may be a photodiode or of the photoconductive or pyroelectric type sensitive, of course, to the emission waveband of the two LEDs which are driven by out-of-phase current pulses or by continuous sine wave signals at different frequencies.

The ratio of the signals derived from the detector 103, which are preferably processed to improve the detected signal to noise ratios thereof, are suitably processed, such that the ratio therebetween is proportional to the concentration of any gas in the sample cell 33.

So that the outputs of the LEDs 1, 2 are time and temperature stable, these two components may be configured separately, as two LED chips in the same structure or as a dual LED chip.

The unit 100 can be used to maintain the stability of the outputs of the two LEDs 1 and 2, such as, by local output monitoring and current drive feedback.

If there was no possibility of the apparatus ageing or suffering contamination or there being any other reason for the parameters of the apparatus to drift, then the intensity measurement provided by the sample beam 22 would provide a substantially accurate concentration measurement.

The basic sample beam only arrangement has been used in the past with a filament bulb as the sample beam source of electromagnetic radiation. However, this known arrangement is suitable only as a detector and not as a measurement or analysis instrument, because its accuracy shifts with time, temperature, condition, contamination and other variable parameters.

The use of a reference beam 12 in the inventive apparatus and method overcomes these problems, because the intensity of the reference beam is not affected by sample gas absorption in the sample cell 33, assuming total absorption of the range of wavelengths in the methane absorption spectrum from the reference beam by the methane gas in the reference cell 13. As a consequence, any change in the intensity of the reference beam 22 of the combined beam 32 passing through the sample cell 33, is due to only environmental influences, such as, contamination by a particulate material, for instance, coal dust in a mine environment or other gases with absorption spectra within the wavelength band of the bees. The sample beam 22 is also subject to substantially the same variation and the change in the reference beam intensity can be measured and the approximate calibration/correction factor applied to the measured intensity of the sample beam 22, thereby rendering the apparatus inherently stabilised, assuming that the outputs from the two LEDs, or other sources of electromagnetic radiation, are both stabilised or are sufficiently stable that they do not affect the measurements provided by the detector 103 and associated circuitry 104, 105.

The intensity of the reference beam 12 can be monitored during the working life of the apparatus and a warning may be given when that intensity falls below a predetermined minimum level. This arrangement provides the apparatus with the ability to provide a warning that it requires servicing, maintenance and/or calibration, a valuable facility in underground applications.

Also, although the out-of-phase arrangement of the reference and sample beams 12, 22 is achieved by driving the respective LEDs 1, 2 out-of-phase with each other, a similar arrangement can be achieved by alternately activating the LEDs.

The apparatus can be modified to operate for any specific absorbing fluid, such as the methane gas used in the preferred embodiment described above with reference to the accompanying drawing, by appropriate choice of the fluid and the appropriate working wavelength.

Also, the sample cell may be constituted by a working or living area in this particular embodiment, a mine chamber.

It is to be appreciated that the invention provides a contamination tolerant apparatus for and method of monitoring, detecting and/or analysing a fluid, such as, a gas and is particularly suitable for use in a mining or high particle-contaminated environment. Also, the invention provides high gas sensitivity with signal processing which may be used to detect low level gas leaks where conventional equipment lacks sufficient sensitivity. In addition, the apparatus and method is intrinsically safe, thus, allowing its use in areas where any explosion hazard is present, for instance, in coal mines, chemical processing and/or gas handling plant or domestic gas leak situations.

Further, it is to be understood that the inventive apparatus and method, as defined above and as described by way of example with reference to the accompanying drawings, can be used to analyse a fluid quantitatively and/or qualitatively.

Moreover, apparatus and method in accordance with the invention may be modified for use with multiple reference beams with respective reference cells. The cells may contain different or mixtures of different gases or different concentrations of different or mixtures of different gases to be detected, monitored or analysed, with each reference beam being passed through the sample cell in combination with the sample beam. Additionally, each reference beam may be modulated in the time or frequency domain in such a way as to allow a beam or beams unaffected by the contents of the sample cell to be isolated, thus enabling the detection, monitoring or analysing of different gases or gas mixtures.

We claim:

1. A fluid presence monitoring apparatus comprising electromagnetic radiation sources arranged to provide respective reference and sample beans of electromagnetic radiation of sinusoidal or pulsed form, a first cell which contains a reference sample of a fluid to be monitored and through which the reference beam of electromagnetic radiation is passable, a second cell which is capable of containing a fluid working sample and through which both the reference and sample beams of electromagnetic radiation are passable, means arranged to detect the reference and sample beams independently of each other after they have passed through the second cell and to provide respective signals representative of the independently-detected beams, and means arranged to compare said signals in order to determine the presence of the fluid to be monitored in the second cell, wherein the electromagnetic radiation sources comprise light emitting diodes whose electromagnetic radiation wavelength is matched with that of the absorption spectrum of the fluid to be monitored.

2. Apparatus as claimed in claim 1, wherein the reference and sample beams are out of phase with each other.

3. Apparatus as claimed in claim 1, wherein the reference and sample beams are of different frequencies.

4. Apparatus as claimed in claim 1, wherein the light emitting diodes are alternately activated to provide respective out-of-phase reference and sample beams.

5. Apparatus as claimed in claim 1, including means arranged to collimate the reference and sample beams and to subsequently combine them after the reference beam has been passed through the reference cell.

6. Apparatus as claimed in claim 1, wherein said detector means comprises a photodiode or photoconductive or pyroelectric detector or any combination thereof.

7. Apparatus as claimed in claim 1, wherein said detector means is a single detector common to both the reference and sample beams.

8. Apparatus as claimed in claim 1, wherein means are arranged to amplify and subsequently enhance the signals representative of the individually-detected reference and sample beams.

9. Apparatus as claimed in claim 1, wherein the sample cell is at least partially filled with any sample fluid by diffusion or pumping or the cell is constituted by a working or living space, such as, a mine gallery, chemical or gas processing/handling plant or room.

10. Apparatus as claimed in claim 1, including a plurality of reference cells through which respective reference beams are passable, the cells containing different gases or mixtures thereof or different concentrations of different or mixtures of different gases.

11. Apparatus as claimed in claim 10, wherein the reference beams are time or frequency modulated.

12. Apparatus as claimed in claim 1, wherein said signal comparison means is arranged to determine also the concentration of any working sample of fluid to be monitored in the second cell.

13. A method of monitoring for fluid presence comprising passing through a first cell containing a reference sample of the fluid to be monitored a reference beam of electromagnetic radiation of sinusoidal or pulsed form, passing through a second cell capable of containing a fluid working sample the reference beam and a sample beam of electromagnetic radiation of sinusoidal or pulsed form, detecting the reference and sample beams independently of each other after they have passed through the second cell, providing respective signals representative of the independently detected beams and comparing said signals to determine the presence of the fluid to be monitored in the second cell, wherein the reference and sample beams are provided by respective light emitting diodes whose electromagnetic radiation wavelength is matched with that of the absorption spectrum of the fluid to be monitored.

14. A method as claimed in claim 13, wherein the reference and sample beams are out of phase with each other.

15. A method as claimed in claim 13, wherein the reference and sample beams are of different frequencies.

16. A method as claimed in claim 13, wherein the light emitting diodes are alternately activated to provide respective out-of-phase reference and sample beams.

17. A method as claimed in claim 13, including collimating the reference and sample beams and subsequently combining them after the reference beam has passed through the reference cell.

18. A method as claimed in claim 13, wherein the reference and sample beams are detected by a photodiode or photoconductive or pyroelectric detector or any combination thereof.

19. A method as claimed in claim 13, wherein the reference and sample beams are detected by a single detector common to both beams.

20. A method as claimed in claim 13, including amplifying, and subsequently enhancing, the signals representative of the individually-detected reference and sample beams.

21. A method as claimed in claim 13, wherein the sample cell is at least partially filled with any sample fluid by diffusion or pumping or the cell is constituted by a working or living space, such as, a mine gallery, chemical or gas processing/handling plant or room.

22. A method as claimed in claim 13, including providing a plurality of reference cells through which respective reference beams are passed, the cells containing different gases or mixtures thereof or different concentrations of different or mixtures of different gases.

23. A method as claimed in claim 22, wherein the reference beams are time or frequency modulated.

24. A method as claimed in claim 13 wherein the concentration of any working sample of fluid to be monitored in the second cell is determined.

\* \* \* \* \*